(12) United States Patent
Cueni et al.

(10) Patent No.: US 7,393,508 B2
(45) Date of Patent: Jul. 1, 2008

(54) VALVE ARRANGEMENT

(76) Inventors: Hansjörg Emil Cueni, Rotzbergstrasse 4, Stansstad (CH); Heiner Scherrer, Grabenackerstrasse 11, Büsserach (CH)

(*) Notice: Subject to any disclaimer, the term of this patent is extended or adjusted under 35 U.S.C. 154(b) by 756 days.

(21) Appl. No.: 10/297,505

(22) PCT Filed: Jun. 8, 2001

(86) PCT No.: PCT/CH01/00357

§ 371 (c)(1),
(2), (4) Date: Jan. 24, 2003

(87) PCT Pub. No.: WO01/94909

PCT Pub. Date: Dec. 13, 2001

(65) Prior Publication Data

US 2003/0185714 A1    Oct. 2, 2003

(51) Int. Cl.
*B01L 11/00*    (2006.01)
(52) U.S. Cl. .................. 422/103; 73/61.56; 73/61.59
(58) Field of Classification Search .................. 422/99, 422/100, 102, 129, 130, 131, 103; 436/180; 73/61.56, 61.59, 863.71, 863.72, 863.73; 137/625, 625.11, 625.12
See application file for complete search history.

(56) References Cited

U.S. PATENT DOCUMENTS

| | | | |
|---|---|---|---|
| 3,201,971 A | 8/1965 | Villalobos | |
| 3,916,465 A | 11/1975 | William | |
| 4,493,476 A * | 1/1985 | Strickland et al. | 251/176 |
| 4,580,759 A * | 4/1986 | Leaseburge et al. | 251/62 |
| 5,295,510 A * | 3/1994 | Bolling et al. | 137/625.48 |
| 6,149,882 A * | 11/2000 | Guan et al. | 422/211 |
| 6,190,619 B1 * | 2/2001 | Kilcoin et al. | 422/131 |
| 6,558,625 B1 * | 5/2003 | Deves et al. | 422/78 |
| 6,605,256 B1 * | 8/2003 | Guller et al. | 422/99 |
| 6,632,404 B1 * | 10/2003 | Freitag et al. | 422/103 |

FOREIGN PATENT DOCUMENTS

| | | |
|---|---|---|
| GB | 890158 | 2/1962 |
| WO | WO0031528 | 6/2000 |

* cited by examiner

*Primary Examiner*—Jill Warden
*Assistant Examiner*—Dwayne K Handy
(74) *Attorney, Agent, or Firm*—Ladas & Parry LLP

(57) ABSTRACT

The valve arrangement comprises a predetermined number of individual valve functionalities, arranged in a manner parallel to each other. A fixed connector plate (3) has a number of sample funnel tubes (6) and output connections (8) for forward transfer of the samples arranged offset from the above. A valve plate (14) with the same number of sample loops (24) for accommodating precisely measured sample amounts may be displaced linearly with respect to the connector plate. In a first position the sample loops are connected to the sample funnel tubes and in a second position with the output connections.

3 Claims, 6 Drawing Sheets

VALVE ARRANGEMENT

The invention relates to a valve arrangement with several individual valve functions arranged parallel to one another.

The majority of valve arrangements conventionally used in analysis at the present time have a number of disadvantages that have an adverse effect on the throughput rate in particular, but also on the precision of the measurement or analysis results obtainable. A further disadvantage is that known valve arrangements are of very complicated construction and therefore susceptible to failure.

The object of the invention is to provide a valve arrangement which does not exhibit said disadvantages.

According to the invention, this is achieved by means of a valve arrangement characterized by the features indicated in claim 1. A preferred embodiment of the invention is described below with the aid of the accompanying drawings, in which:

Figure 1:
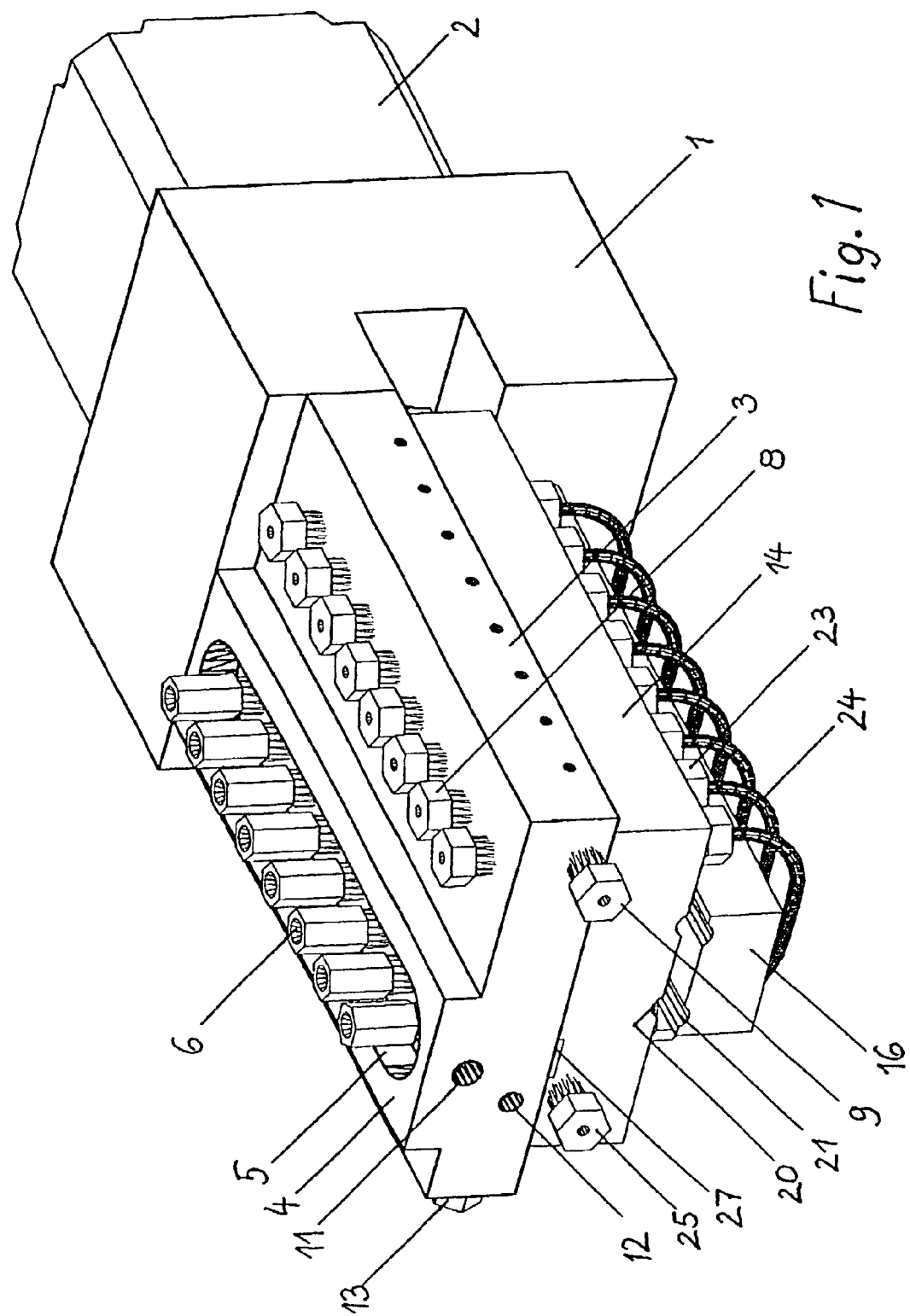
FIG. 1 is a perspective view of a valve arrangement according to the invention.

The valve arrangement shown in FIG. 1 is an eight-way valve and consists of a support 1 in the form of a block or plate, to which the other parts of the valve arrangement are fixed and which in turn is fixed in an analytical instrument or the like. The support is made of aluminium. Attached to one side of the support 1 is a step motor 2 for driving or switching the valve. Firmly attached to the opposite side of the support 1 is a horizontal plate 3 on which the essential input and output connections of the valve arrangement are located and which is therefore referred to hereafter as the connector plate. The connector plate is made of a chemically inert material, e.g. chrome steel.

On one side of the surface of the connector plate 3, in a platform 4 that projects upwards, there is a trough 5 in which eight sample funnel tubes 6 for sample injection are arranged at the same distance from one another. The distance between the funnels 6 is identical to the well spacing of microtitre plates so that the eight cannulas of an eight-way pipette or syringe can simultaneously inject the samples taken from one row of a microtitre plate into the eight sample funnel tubes. The sample funnel tubes are located in the upper part of drilled holes which lead through the connector plate to its flat underside.

An attachment 7, whose function is illustrated in greater detail below, is provided on the platform 4 for raising the side walls of the trough.

On the other side of the surface of the connector plate 3 a row of eight output connections 8 is arranged, parallel to the row of sample funnel tubes 6, in eight drilled holes leading through the plate to its underside. The connections 8 are designed as high-pressure connections and are used for coupling to lines which, depending on the use of the valve arrangement, lead individually to a number of detectors or via a selector valve to one detector, for example a mass spectrometer, as explained in greater detail below.

The row of output connections 8 is offset in the longitudinal direction relative to the row of sample funnel tubes 6 by a distance which is less than the well spacing of microtitre plates. The offset is 2 mm in the present case. This distance corresponds to the valve lift, as shown below.

Figure 5:
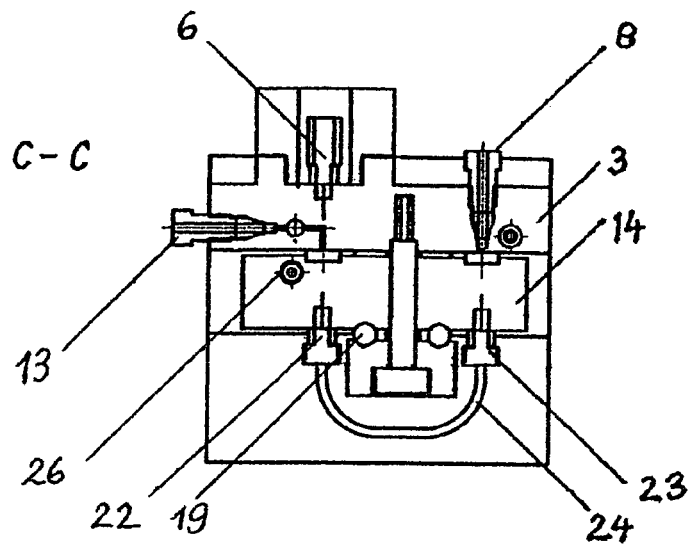
FIG. 5 shows a cross-section along C-C in FIG. 2.

Located on the front side of the connector plate 3 are a further connection 9 and two drilled holes 11, 12. The connection 9 sits in the mouth part of a drilled hole 10 running longitudinally through the connector plate 3 (cf. FIGS. 5-7), which hole 10 combines with transverse drilled holes to form an overflow system and can be coupled via the connection 9 to a waste receptacle.

The upper drilled hole 11 leads from inside the trough 5 to the outside and also serves as a connection to an overflow system for flushing liquid from the trough into a waste receptacle. As explained in greater detail below, a larger amount of flushing liquid accumulates in the trough, so a line of larger dimensions has to be connected to the hole 11.

The drilled hole 12 runs inside the connector plate over the entire length and, as shown below, combines with a number of transverse drilled holes to form a solvent pressure line, i.e. a feed system for solvent which is normally fed by a high-pressure pump, depending on the application. On the far side face of the connector plate 3 in FIG. 1, there is another connection 13 which, with two further connections, forms part of said feed system for the solvent conveyed under pressure.

Figure 2:
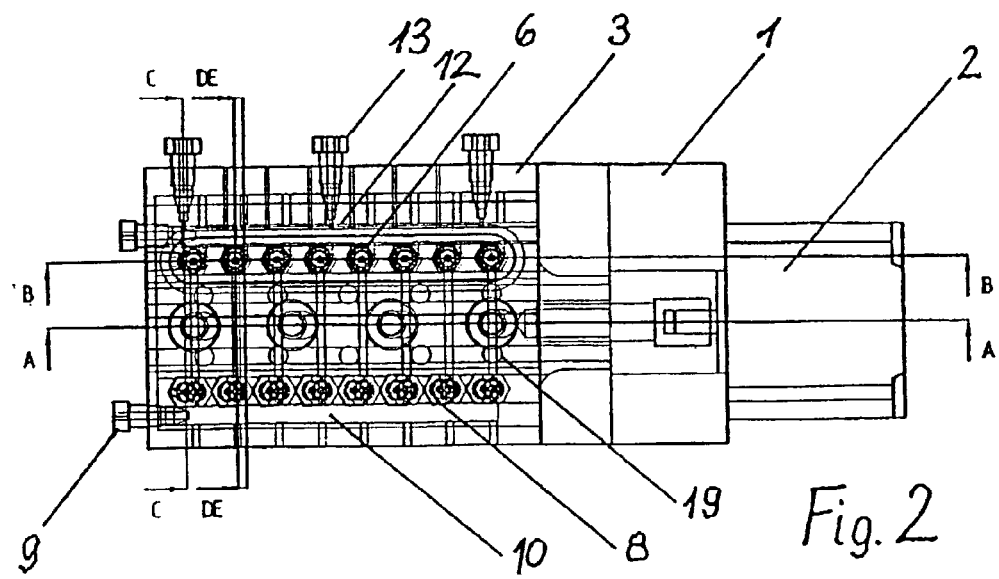
FIG. 2 is a top view of the valve arrangement of FIG. 1 in one position of the valve plate.

The top view of FIG. 2 shows the offset of the sample funnel tubes 6 and the output connections 8. The three connections 13 forming part of the solvent pressure line 12 are also shown.

Other connecting channels running inside the connector plate 3 are shown in the various sectional drawings of FIGS. 4-7 and are explained in the description below. Arranged underneath the connector plate 3 is a valve plate 14 in the form of a slide or carriage, which is moved to and fro between two positions in the longitudinal direction, relative to the connector plate 3, by the step motor 2.

Figure 3:
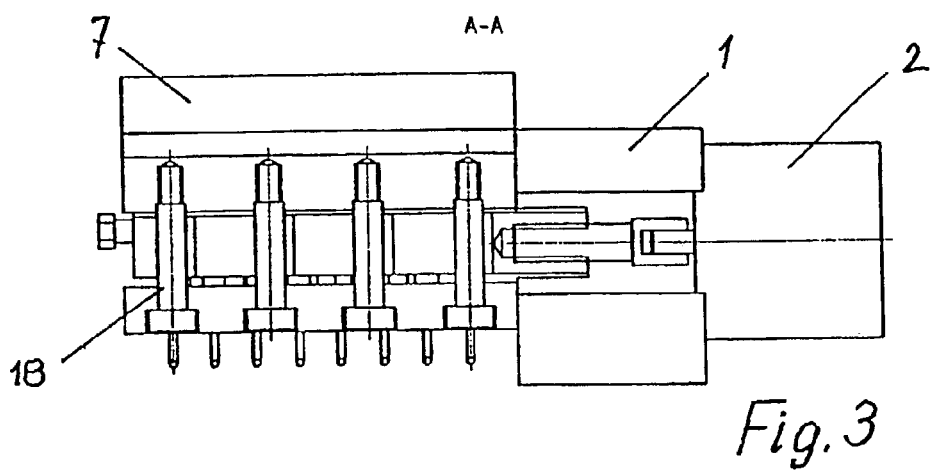
FIG. 3 shows a longitudinal section along A-A in FIG. 2.

Underneath the valve plate there is a bearing plate 16 firmly joined to the connector plate 3. FIG. 3 shows how the bearing plate 16 is fixed to the connector plate 3 by means of screws 18. Arranged between the bearing plate 16 and the valve plate 14 is a ball bearing consisting of balls 19 housed in two upper parallel grooves 20 running over the entire length of the underside of the valve plate 14, and corresponding lower grooves 21, in the surface of the bearing plate 16.

On its underside the valve plate is provided with two rows 22, 23 of eight high-pressure connections which sit in the lower part of drilled holes running right through the valve plate to its surface. One of the two rows of connections 22 lies in a plane with the funnel tubes 6 and the other row of connections 23 lies in a plane with the output connections 8. The individual connections within the two rows are the same distance apart as the sample funnel tubes or the output connections, i.e. the distance between the sample receptacles, or the well spacing, of the microtitre plate. In contrast to those in the connector plate 3, the two rows of connections 22, 23 in the valve plate are not offset relative to one another in the longitudinal direction.

The pairs of opposite connections in the two rows are coupled together by arc-shaped lines of exactly equal length running underneath the bearing plate, which constitute sample loops 24. The sample loops 24 accommodate precisely measured amounts of sample, which are conveyed to a detector.

Located on the front side of the valve plate 14 is a high-pressure connection 25 which sits in the mouth of a drilled hole 26 running almost the entire length of the valve plate. The hole 26 (cf. FIGS. 5-7) combines with transverse drilled holes to form a flushing line, i.e. a system for conveying flushing liquid to the funnel tubes in one of the two valve positions, as illustrated in greater detail below.

Located in the upper face of the valve plate, in the region of the mouths of the drilled holes belonging to the rows of connections 22, 23, are sealing strips 27 arranged in two parallel slots, which, by means of the pressure with which the valve plate acts against the connector plate 3 via the screws joining the bearing plate 16 to said connector plate 3, reliably isolate the individual channels from one another.

The two positions which the valve plate can adopt correspond to said longitudinal offset between the sample funnel tubes 6 and the output connections 8. This offset is 2 mm in the present embodiment. Thus the two rows of connections 22, 23 in the valve plate can be brought in line with, i.e. coupled to, either the sample funnel tubes 6 or the output connections 8. This is illustrated in greater detail below with the aid of the sectional drawings of FIGS. 4-7.

Figure 4:
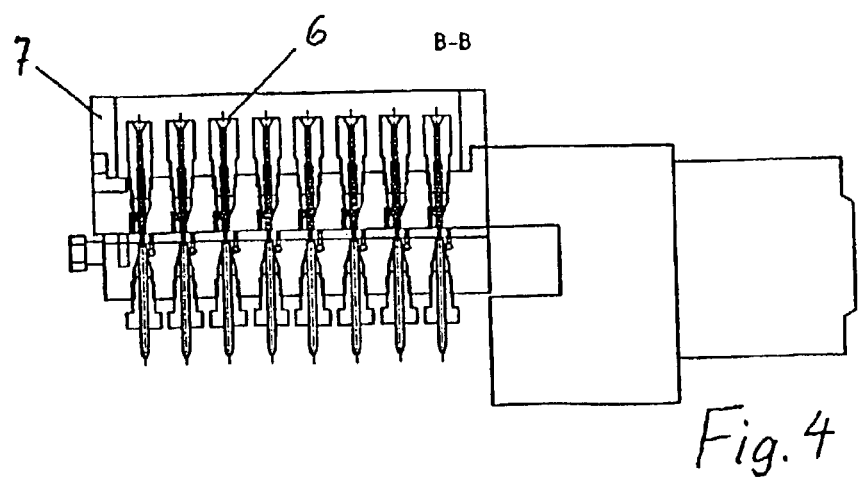
FIG. 4 shows a longitudinal section along B-B in FIG. 2.

In the position of the valve plate 14 shown in longitudinal section in FIG. 4, the sample funnel tubes 6 are coupled to the row of connections 22 of the sample loops 24. At the same time the mouths of the flushing line 26 at the contact face between the connector plate and the valve plate are closed. This can also be seen in the cross-sections of FIGS. 5-8, which additionally show the situation on the other side, i.e. with the output connections and the row of connections 23. The section C-C of FIG. 5 runs through the median plane of the first transverse drilled hole of the solvent pressure line, which is coaxial with one of the external connections 13. The channel leading to the contact face is closed in this position. Located on the other side in this cutting plane is the axis of the first output connection 8, whose mouth on the underside of the connector plate is likewise closed.

Figure 6:
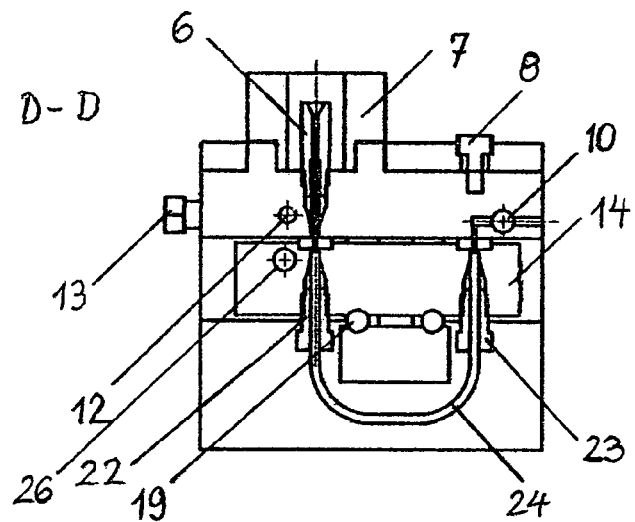
FIG. 6 shows a cross-section along D-D in FIG. 2.

The section D-D of FIG. 6 runs through the axis of the second sample funnel tube and shows that this funnel is coupled to the corresponding connection of the row 22 in the valve plate. On the other side of the loop, the corresponding connection of the row 23 is coupled to the overflow system. Thus, in this position, a sample can be injected into the sample funnel tube, thereby filling the sample loop. Excess sample passes into the overflow system. As all eight sample funnel tubes 6 are similarly coupled to the sample loops in this position, all eight sample loops can be filled simultaneously.

Figure 7:
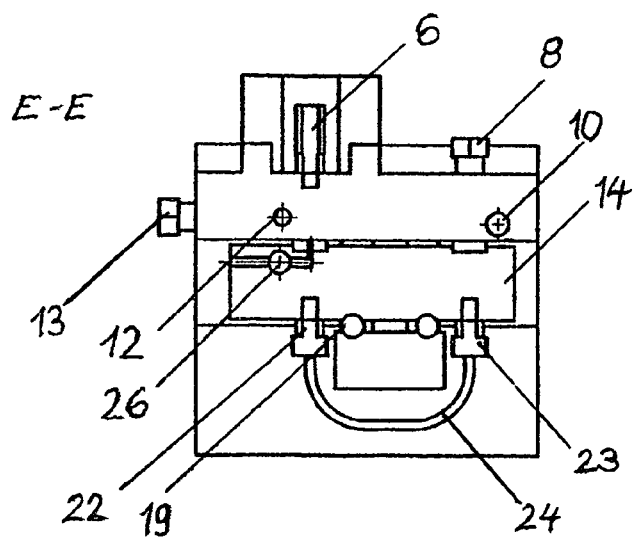
FIG. 7 shows a cross-section along E-E in FIG. 2.
Figure 8:
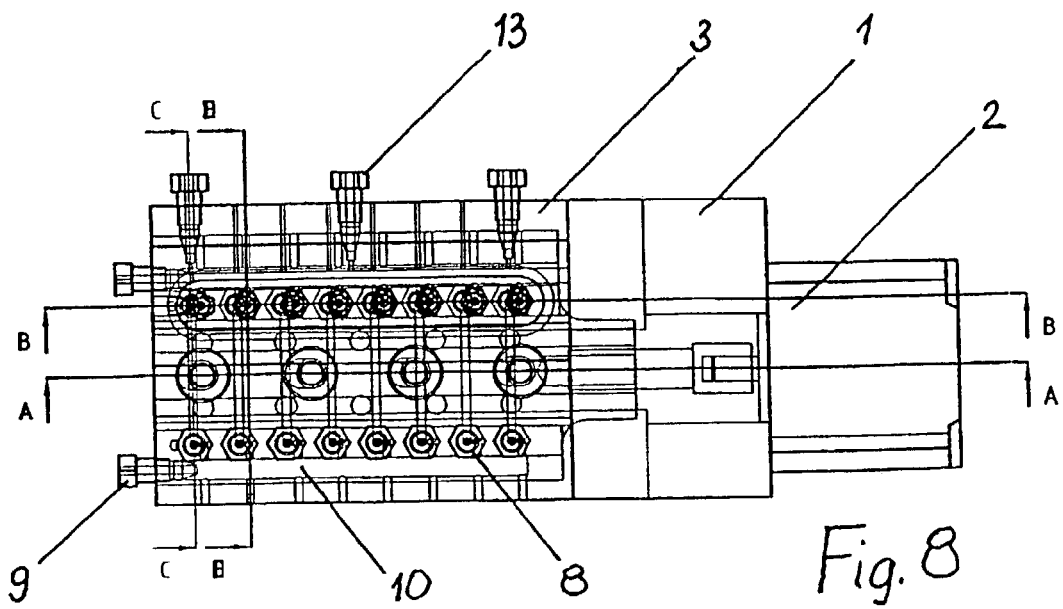
FIG. 8 is another top view of the valve arrangement in the second position of the valve plate.
Figure 9:
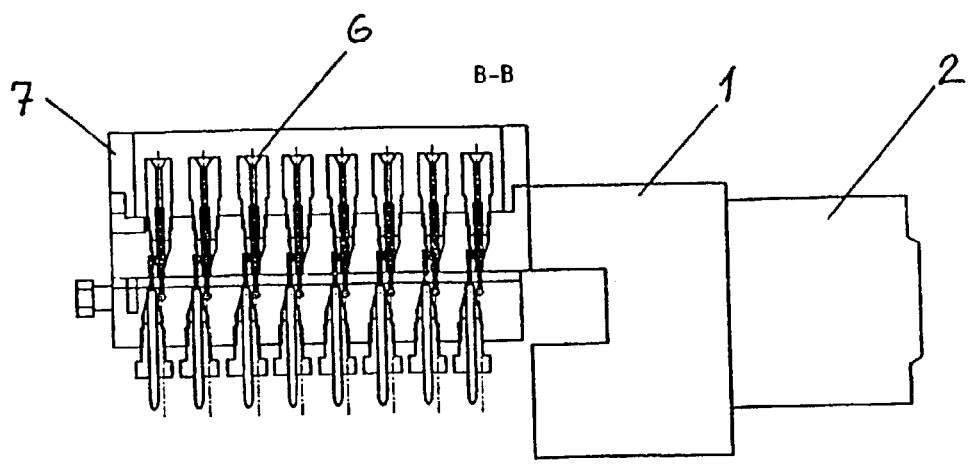
FIGS. 9-11 show the sections A-A, C-C and D-D in the second position.
Figure 10:
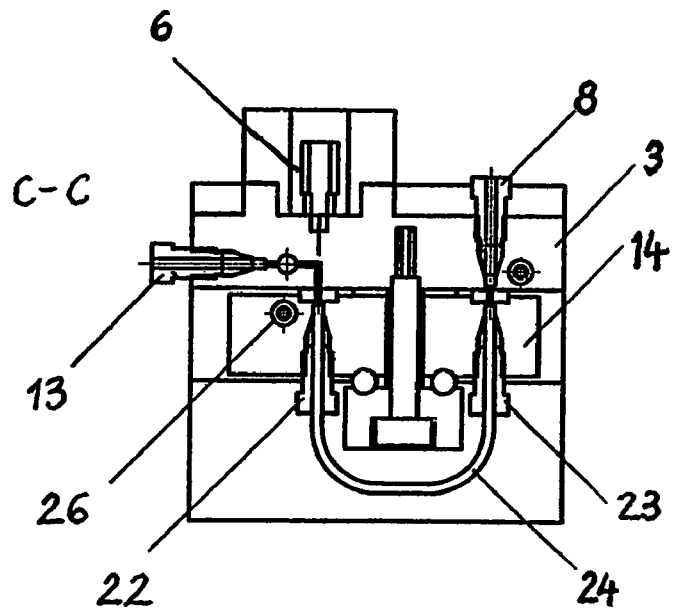

Finally, the section E-E of FIG. 7 shows that, in this position, the flushing system at the contact face between the connector plate 3 and the valve plate 14 is also closed.

The situation in the second position of the valve plate is shown in FIGS. 8-11. It can be seen in the top view of FIG. 8 that the output connections 8 now coincide with the row of connections 23, while the sample funnel tubes 6 do not coincide with the row of connections 22. This can be seen in the longitudinal section A-A of FIG. 9. The row of connections 22 are now coupled to the pressure line 12. The cross-section C-C running through the first transverse drill hole in the pressure line (cf. FIG. 5) shows in FIG. 10 that the first sample loop is coupled to the pressure system and on the other side to the output connection. Thus, in this position, the output connection 8 is coupled to a detector.

Figure 11:
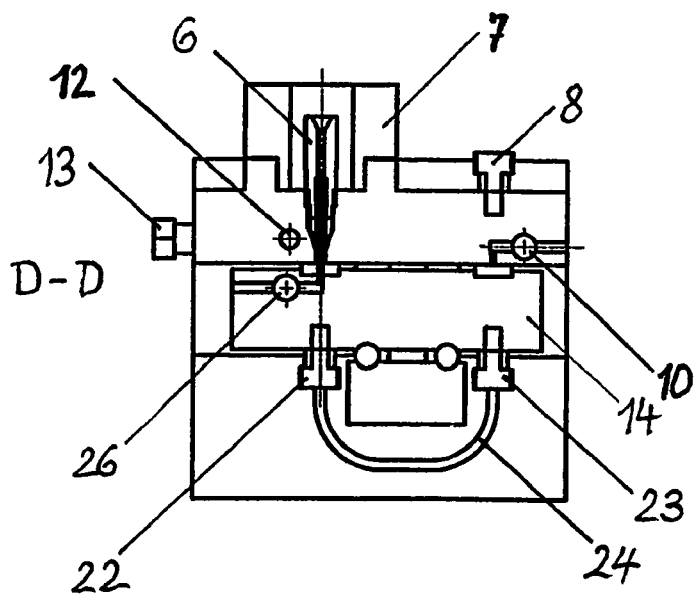

At the same time, as can be seen in the section D-D of FIG. 11, the sample funnel tubes 6 are coupled to the flushing system. The solvent fed through the flushing system flushes the sample funnel tube. The cannulas are also flushed at the same time and it is for this purpose that they remain in the filling position until the flushing process has ended. The flushing process is terminated before the sampling sequence so that the eight-way syringe can be refilled and brought into the injection position. As soon as sampling has ended, the valve plate is switched back to the first position, in which the sample loops are immediately filled with the next samples.

Figure 12A:
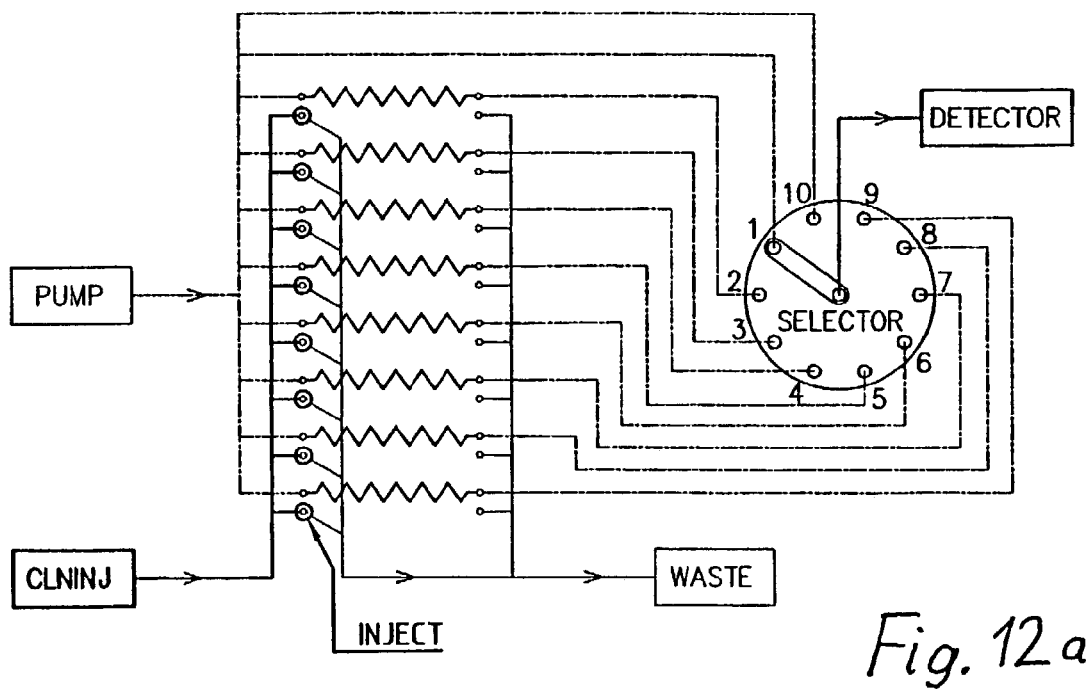
FIGS. 12a and 12b show a flow diagram of one possible use of the valve arrangement together with a selector valve.

One possible use of the valve arrangement is shown in the flow diagram of FIG. 12*a,b*. The valve arrangement according to the invention works together with a commercially available selector valve. The output connections 8 are coupled via individual lines to the individual inputs 1-10 of the selector. The output of the selector is coupled to a detector, for example a mass spectrometer. The solvent pump is coupled simultaneously to the solvent pressure line 12 and to at least one individual input of the selector.

As already described, in the first position of the valve arrangement according to the invention, illustrated in FIG. 12*a*, the sample funnel tubes 6 are coupled via the sample loops 24 to the overflow system. In this position eight samples are applied simultaneously by means of an eight-way syringe, which is indicated by the functional description "INJECT". Excess sample passes via the overflow system to a receptacle indicated by "WASTE". The connections of the solvent pressure line are closed in this position of the valve arrangement. The connections of the flushing line are likewise closed. On the other hand, there is a connection between the pump and the selector so that pure solvent is fed to the mass spectrometer for making a blank measurement.

Figure 12B:
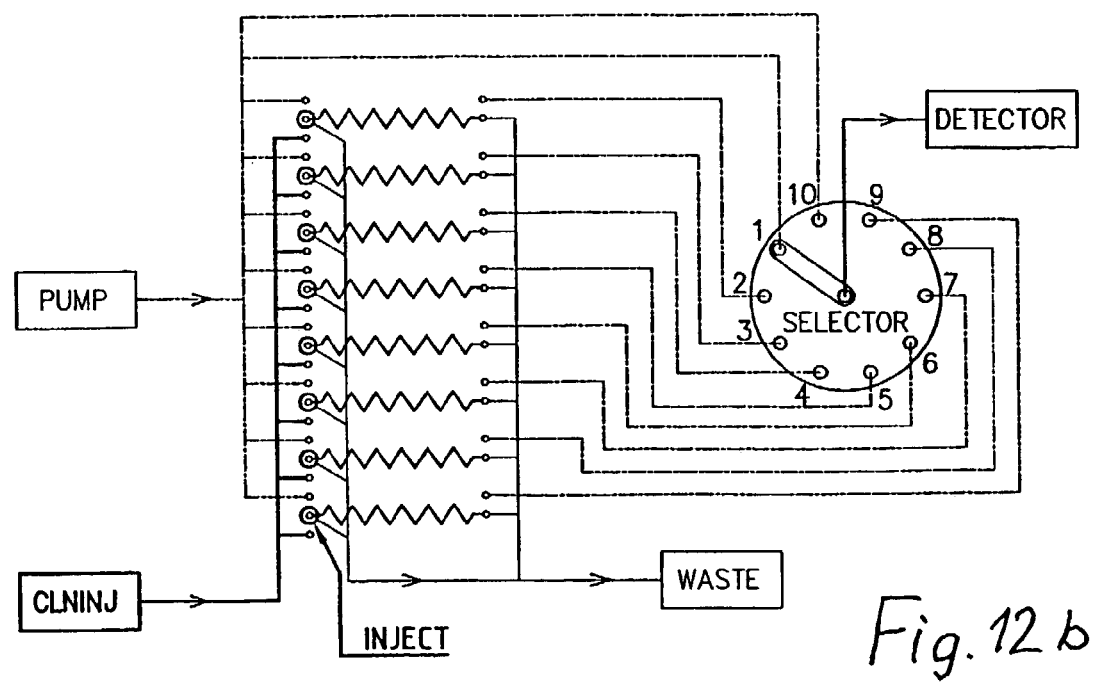

The second position, shown in FIG. 12*b*, couples the solvent pressure line to the sample loops and their output connections to the selector valve. By continuing to switch to positions 1-10, the selector valve can successively bring the individual samples into the sample loops and deliver them to the mass spectrometer.

During this procedure, flushing of the sample funnel tubes 6 and the syringe cannulas is taking place on the input side of the valve according to the invention. The sample funnel tubes 6 are coupled to the flushing system indicated by "CLNINJ". The flushing liquid flows out of the trough 5 into the "WASTE". When the last sample loop has been evacuated into the mass spectrometer, the input side is ready for the next sample application, which takes place almost immediately. Thus, after only a very short delay, the selector valve can deliver the next sample to the mass spectrometer.

In this way the mass spectrometer receives an uninterrupted sequence of samples with a negligible delay between each block of eight, affording a throughput rate never previously achieved.

The invention claimed is:

1. A valve arrangement with a given number of individual valves arranged parallel to one another, comprising a fixed connector plate with the same given number of sample funnel tubes and the same given number of output connections, offset relative to the sample funnel tubes, for conveying the samples, and a valve plate provided with the same given number of sample loops for accommodating precisely measured amounts of the samples, said valve plate being capable of linear displacement between a first position, in which the sample loops are coupled to the sample funnel tubes, and a second position, in which the sample loops are coupled to the output connections.

2. The valve arrangement according to claim 1, wherein, in the first position of the valve plate, the sample loops are coupled on the output side to an overflow line.

3. The valve arrangement according to claim 1, wherein, in the second position of the valve plate, the sample loops are coupled on the input side to a solvent pressure line and at the same time the sample funnel tubes are coupled to a flushing system.

* * * * *